United States Patent [19]

Theeuwes et al.

[11] 4,016,880
[45] Apr. 12, 1977

[54] OSMOTICALLY DRIVEN ACTIVE AGENT DISPENSER

[75] Inventors: Felix Theeuwes, Los Altos; Nalinkant C. Damani, Sunnyvale, both of Calif.

[73] Assignee: Alza Corporation, Palo Alto, Calif.

[22] Filed: Mar. 4, 1976

[21] Appl. No.: 663,665

[52] U.S. Cl. .............................. 128/260; 128/130
[51] Int. Cl.² ....................................... A61M 31/00
[58] Field of Search ............ 128/260, 130; 424/15, 424/19, 22, 35

[56] References Cited

UNITED STATES PATENTS

| | | | |
|---|---|---|---|
| 2,478,182 | 8/1949 | Consolazio | 424/22 |
| 3,146,169 | 8/1964 | Stephenson | 424/22 X |
| 3,247,066 | 4/1966 | Milosovich, Jr. | 424/19 |
| 3,538,214 | 11/1970 | Polli | 424/19 |
| 3,916,899 | 11/1975 | Theeuwes | 128/260 |
| 3,971,376 | 7/1976 | Wichterle | 128/260 |
| 3,977,404 | 8/1976 | Theeuwes | 128/260 |

Primary Examiner—Aldrich F. Medbery
Attorney, Agent, or Firm—Thomas E. Ciotti; Paul L. Sabatine; Edward L. Mandell

[57] ABSTRACT

Osmotically driven active agent dispenser for use in an aqueous environment that pumps a solution of active agent, such as a drug, at a predetermined, constant rate. The dispenser is in the form of a coated tablet comprising: a core of an osmotically effective active agent composition; and an inexpandable wall that encloses the core, has a controlled permeability to water and includes means, such as brittleness or sites of structural weakness, that is responsive to the pressure generated within the dispenser by imbibition of water from the environment by the core through the wall to form at least one, and usually many, passageways in situ in the wall through which the active agent composition in solution is pumped osmotically at a rate that is substantially dependent of the rate at which water is being imbibed into the dispenser.

11 Claims, 1 Drawing Figure

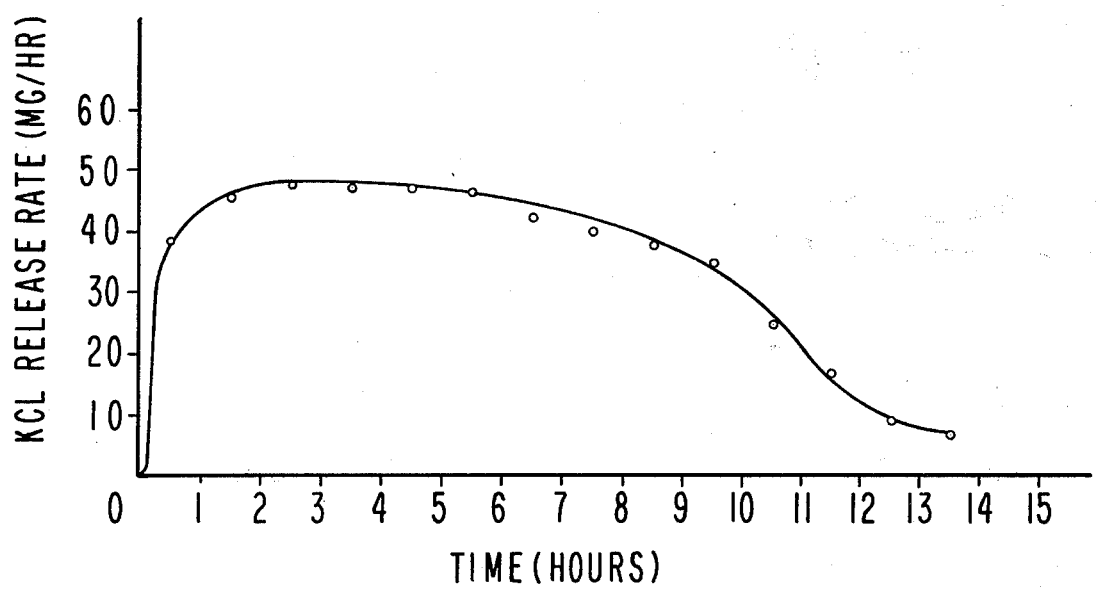

OSMOTICALLY DRIVEN ACTIVE AGENT DISPENSER

BACKGROUND OF THE INVENTION

1. Field of the Invention

This invention relates to an osmotically driven active agent dispenser.

2. Description of the Prior Art

The invention is a modification of the osmotically driven active agent dispenser disclosed in U.S. Pat. No. 3,916,899. Briefly, the patented dispenser comprises: a core of an osmotically effective active agent composition; a water insoluble wall that is impermeable to the composition, has a controlled permeability to water and encloses the core; and one or more particularly sized passageways extending through the wall to the core. When placed in an aqueous environment, such as the gastrointestinal tract, eye, vagina, and uterus, water is imbibed from the environment by the composition through the wall causing the composition to be dissolved, a pressure gradient between the interior and exterior of the dispenser to be generated, and the dissolved composition to be pumped out the passageway(s) into the environment. The release of active agent from these dispensers is continuous, sustained, predetermined, and substantially constant over a major portion of the release period. The patent discloses that the passageways in the wall may be formed mechanically, such as by drilling, or in situ by erosion of a bioerodible component incorporated into the wall.

Commonly owned U.S. application Ser. No. 578,979 filed May 19, 1975 discloses a drug dispenser in the form of a unit body of a mixture of discrete particulate depots of an osmotically effective drug composition dispersed in a water insoluble, water permeable polymer. The depots imbibe water from the environment serially beginning with those nearest the exposed surface of the body until enough pressure is generated within the depots to cause them to burst open. As the depots burst open the drug composition within them is released.

U.S. Pat. No. 2,478,182 describes salt tablets comprised of compressed salt granules coated with cellulose acetate or cellulose nitrate. According to the patent the cellulose derivative penetrates the compressed granules to form a honeycomb structure. Upon ingestion of the tablets, water dialyzes into the compartments of the honeycomb and salt dialyzes out. The patent also says the honeycomb compartments burst when they become engorged with water.

U.S. Pat. No. 3,247,066 describes medicinal beads that burst to release medicine. The beads consist of a core of a water swellable colloid containig a drug that is coated with a polymer that is water permeable and inert to gastrointestinal fluids. When the beads are ingested, water diffuses inwardly through the coating to swell the colloid core. This swelling creates sufficient pressure to burst the coating, whereby the entire quantity of drug in the core is released.

Also, the agricultural chemical art literature describes various slow release formulations of fertilizer or pesticide and polymer. For instance, U.S. Pat. No. 3,708,276 describes grains of fertilizer that are coated with water insoluble resins containing foreign particles. The presence of such particles is said to affect the permeability and the rate at which the fertilizer is eluted.

SUMMARY OF THE INVENTION

The invention is an osmotically driven active agent dispenser for use in an aqueous environment comprising: a core of an osmotically effective active agent composition, and a substantially inexpandable wall enclosing the core, the wall having a controlled permeability to water and including means responsive to the pressure generated within the dispenser by imbibition of water from the environment by the core through the wall to form at least one passageway in situ in the wall through which the active agent composition in solution is pumped osmotically into the environment at a substantially predetermined, substantially constant rate that is dependent upon the rate at which water is being imbibed into the dispenser.

BRIEF DESCRIPTION OF THE DRAWING

The drawing is a graph of the active agent release pattern of the dispensers of the example set forth below. The graph plots release rate versus time.

DETAILED DESCRIPTION OF THE INVENTION

As indicated above, the dispenser of this invention is a unique modification of the dispenser of U.S. Pat. No. 3,916,899. The difference between the patented dispenser and the present dispenser is that the present dispenser does not have a preformed passageway or a bioerodible wall component that erodes in situ to form a passageway, but instead its wall includes means that is responsive to the osmotically generated pressure within the dispenser to form at least one and usually many passageways in situ in the wall. These passageways serve the same function as the preformed or in situ erosion formed passageway of the patented dispenser.

The terms "aqueous environment", "active agent", "drug", "osmotically effective", and "wall" used herein have generally the same meanings as in U.S. Pat. No. 3,916,899 and the respective descriptions of those terms that appear in the patent are incorporated herein by reference. Also the form and utility of the invention dispenser may be the same as that of the patented dispenser and the portions of the patent disclosure pertaining thereto are incorporated herein by reference. Likewise, the materials that are used to form the wall, the characteristics (except for the passageway forming means) of the wall, and the procedures used to form the core and enclose it within the wall may be the same as those of the patent and the disclosure of the patent that is relevant to these items is incorporated herein by reference.

As in the patented dispenser, the active agent composition that forms the core of the invention dispenser is an osmotically effective solute. In this regard the composition may be agent that itself is such a solute and that is neat or formulated with a carrier that may or may not also be such a solute, or agent that is not such a solute formulated with a carrier that is such a solute. In its osmotically effective solute role, the composition imbibes water from the environment inwardly through the wall of the dispenser. The imbibed water dissolves the composition and a hydrostatic pressure difference is established across the wall between the solution of active agent composition and the aqueous environment. The magnitude of and the rate of generation of this difference will depend upon the solubility of the composition in water, the number of ionic species it produces in solution, and the concentration gradient across the wall. The difference must be sufficient to activate the passageway forming means of the wall. Once the passageways are formed by the means, water is imbibed continuously into the dispenser in response to the osmotic pressure gradient across the wall. The imbibed water in turn continuously forces the solution of composition out the passageway(s) into the environment. Accordingly the solute should generate a significantly higher osmotic pressure in solution than the osmotic pressure of the aqueous environment in which the dispenser is used. For instance in embodiments that release drugs into body fluids solutes that exhibit a significantly higher osmotic pressure than such fluids (i.e. significantly higher than about 750 kPa) must be used. Solutes that exhibit osmotic pressures in the range of about 20,000 to about 40,000 kPa will normally be used in such drug dispensing embodiments. Osmotic pressure may be measured with a commercially available osmometer that measures the vapor pressure difference between pure water and the composition solution. The vapor pressure ratio may be converted into osmotic pressure difference by standard thermodynamic calculations.

The wall of the invention dispenser is substantially inexpandable as is the wall of the patented dispenser. This means that there is no substantial increase in the volume of the core before or during the dispensing period despite imbibition of water.

The passageway forming means of the wall may be an inherent property of the wall, such as the brittleness of the polymer forming the wall, or it may be sites of structural weakness in the wall such as might be caused by: incorporating foreign materials, e.g., fillers, in the polymer forming the wall; using a blend of incompatible polymers to make the wall; or, depending on the wall material, post-treating the wall thermally, by solvent crazing, or by irradiation. Inherent properties of the wall material that constitute such means may be a result of the composition of the wall (such as in the case of a polymer its crystallinity, molecular weight, degree and nature of cross-linking, and the presence and structure of side groups on the polymer backbone) and/or the manner in which the wall is formed.

The passageways formed by the means will generally be irregularly shaped, sized, and positioned and may be in the form of discrete holes or a network of cracks or fissures extending over part or all of the dispenser surface. Individually the passageways are normally minute, usually microscopic, and they constitute an outlet for the solution of active agent that falls within the maximum and minimum size limitations described in columns 20–21 of U.S. Pat. No. 3,916,899.

In the dispensers of the invention, the thickness of the wall may affect the operability of the passageway forming means and in such instances wall thickness will be correlated with the particular passageway forming means to insure that one or more passageways meeting the abovementioned minimum/maximum size limitations are formed timely. Normally the thickness of the wall will be in the range of about 100 to about 500 microns.

Active agent is released from the invention dispensers as follows. Upon placement of the dispenser in an aqueous environment, water is imbibed through the wall by the core of active agent composition. Since the wall is substantially inexpandable the imbibed water will cause a build up of pressure within the dispenser. During this build up there is no release of composition by osmotic pumping. The pressure builds up until it is sufficient to activate the passageway forming means of the wall. For instance if the brittleness of the wall is the means, the pressure has built up to the point at which brittle failure is initiated and the wall cracks. Alternatively, in instances in which there are sites of structural weakness in the wall the pressure has built up to the point at which stress fracture occurs at such a site or sites. The magnitude of this threshold pressure will vary with the particular means involved and the thickness of the wall. Desirably it will be relatively low, that is in the range of about 50 to about 5000 kPa. Once the passageway(s) is/are formed the pressure is relieved and osmotic pumping of the solution begins. After a short period of time, steady state conditions are reached and the solution of active agent composition is being pumped out of the in situ-formed passageway(s) at a substantially constant rate. The magnitude of the constant rate is dependent primarily upon the rate of water imbibition into the dispenser and is independent of the size of the passageway(s), provided such size is within the above-described maximum/minimum size limitations. This substantially constant rate prevails over the major portion of the dispensing period. After the active agent composition has been depleted to the extent that a saturated solution of composition is not maintained within the dispenser, the rate of release begins to tail off, decreasing continuously as the concentration of active agent in solution within the dispenser decreases.

EXAMPLE

The following example illustrates an embodiment the invention that may be used to dispense the drug potassium chloride. This example is not intended to limit the invention in any manner. Unless indicated otherwise, percentages are by weight.

Cores of potassium chloride containing 5% FD&C Blue No. 1 water soluble dye in the form of compressed tablets were made using a Manesty rotary tableting machine with 0.95 cm diameter standard concave punches set to a hardness of 8 kg. A mixture of cellulose acetate (sold by Eastman Kodak under the designation E-320) of 32% acetyl content and the water insoluble aluminum lake dye FD&C Yellow No. 5 in a 99:1 weight ratio was made up as a 5% solution in acetone/water (88.5%/11.5%). This solution was deposited on the potassium chloride cores using a Wurster air suspension apparatus to form a 125 micron thick wall or membrane about each core.

The theoretical steady state potassium chloride release rate from the coated tablets was calculated to be 45 mg/hr, based on a wall surface area of 2.3 cm$^2$, a KCl solubility of 360 mg/ml, and a wall water transmission of 0.27 cm$^3$ mil/cm$^2$ hr. The formulas appearing in col 18 et seg. of U.S. Pat. No. 3,916,899 were used to make these calculations.

Five of the coated tablets were placed in known quantities of water at 37° C. After a short time a passageway/passageways was/were formed in each tablet at a site/sites of structural weakness in the tablet wall caused by the presence of the yellow dye, as evidenced by the appearance of a blue spot/spots on the walls of the tablets. Aliquots of the water were taken at one hour intervals beginning ½ hour after the tablets were placed in the water. The KCl content of each aliquot was determined by standard KCl analysis techniques. From these determinations KCl rates from the tablets were calculated. The average release rate from the five tablets plotted against time is shown in the accompanying drawing. As illustrated in the drawing the in vitro release rate between hours 1 and 9 was substantially constant and corresponded approximately with the predicted, theoretical rate.

Modifications of the invention dispenser that are obvious to those skilled in the pharmaceutical and/or chemical arts are intended to be within the scope of the following claims.

We claim:

1. An osmotically driven active agent dispenser for use in an aqueous environment comprising:
   a. a core of an osmotically effective pressure generating active agent composition; and
   b. a substantially inexpandable wall having a substantially intact surface enclosing the core, said wall being substantially impermeable to the active agent composition and having a controlled permeability to water and including,
   c. means responsive to the pressure generated within the dispenser by imbibition of water from the environment by the core through the wall to create and form at least one exit passageway in situ in the wall through which the active agent composition in solution is pumped osmotically from the core into the environment at a substantially predetermined, substantially constant rate.

2. The dispenser of claim 1 wherein the active agent composition in solution exhibits an osmotic pressure that is significantly greater than the osmotic pressure of the aqueous environment.

3. The dispenser of claim 1 wherein the active agent is a drug.

4. The dispenser of claim 3 wherein the composition in solution exhibits an osmotic pressure of about 20,000 to about 40,000 kPa.

5. The dispenser of claim 1 wherein the wall is about 100 to about 500 microns thick.

6. The dispenser of claim 1 wherein the means is an inherent property of the material forming the wall.

7. The dispenser of claim 1 wherein the means is sites of structural weakness in the wall.

8. The dispenser of claim 7 wherein the sites are the result of incorporating a foreign material into the material forming the wall, forming the wall from mutually incompatible polymers, treating the wall thermally, solvent crazing the wall, or subjecting the wall to irradiation.

9. The dispenser of claim 1 wherein there is more than one passageway and the passageways are irregularly shaped, sized, and positioned.

10. The dispenser of claim 1 wherein the passageway is in the form of a network of cracks extending over at least a part of the surface of the dispenser.

11. The dispenser of claim 1 wherein the passageway is in the form of a plurality of discrete holes.

* * * * *

REEXAMINATION CERTIFICATE (51st)

United States Patent [19]

Theeuwes et al.

[11] B1 4,016,880

[45] Certificate Issued Feb. 1, 1983

[54] OSMOTICALLY DRIVEN ACTIVE AGENT DISPENSER

[75] Inventors: Felix Theeuwes, Los Altos; Nalinkant C. Damani, Sunnyvale, both of Calif.

[73] Assignee: Alza Corporation, Palo Alto, Calif.

Reexamination Request
No. 90/000,087, Oct. 14, 1981

Reexamination Certificate for:
Patent No.: 4,016,880
Issued: Apr. 12, 1977
Appl. No.: 663,665
Filed: Mar. 4, 1976

[51] Int. Cl.³ .......................................... A61M 31/00
[52] U.S. Cl. .................................. 128/260; 128/130
[58] Field of Search ...................................... 128/260

[56] References Cited

U.S. PATENT DOCUMENTS

| | | | |
|---|---|---|---|
| 2,478,182 | 8/1949 | Consolazio | 424/22 |
| 3,146,169 | 8/1964 | Stephenson | 424/22 X |
| 3,247,066 | 4/1966 | Milosovich, Jr. | 424/19 |
| 3,538,214 | 11/1970 | Polli | 424/19 |
| 3,916,899 | 11/1975 | Theeuwes | 128/260 |
| 3,971,376 | 7/1976 | Wichterle | 128/260 |
| 3,977,404 | 8/1976 | Theeuwes | 128/260 |

FOREIGN PATENT DOCUMENTS

1093286   11/1967   United Kingdom.

*Primary Examiner*—C. Fred Rosenbaum

[57] ABSTRACT

Osmotically driven active agent dispenser for use in an aqueous environment that pumps a solution of active agent, such as a drug, at a predetermined, constant rate. The dispenser is in the form of a coated tablet comprising: a core of an osmotically effective active agent composition; and an inexpandable wall that encloses the core, has a controlled permeability to water and includes means, such as brittleness or sites of structural weakness, that is responsive to the pressure generated within the dispenser by imbibition of water from the environment by the core through the wall to form at least one, and usually many, passageways in situ in the wall through which the active agent composition in solution is pumped osmotically at a rate that is substantially dependent of the rate at which water is being imbibed into the dispenser.

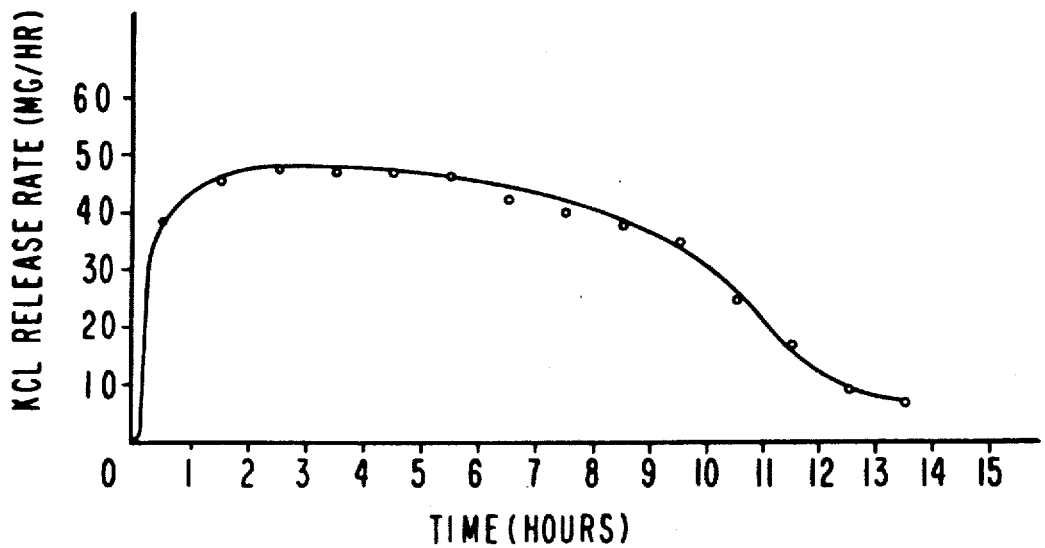

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, paragraph 2.

The wall of the invention dispenser is substantially inexpandable as is the wall of the patented dispenser. This means that there is no substantial increase in the volume of the core before or during the dispensing period despite imbibition of water. *The wall of the dispenser is comprised in total or at least a part of a film forming semipermeable membrane that possesses permeability to an external fluid while simultaneously being essentially impermeable to the active agent composition that forms the core. Thus, the dispenser defined by the wall can be of unit construction, or composite construction with a section of a semipermeable membrane either formed integral in the wall or optionally lined or laminated to the wall. The semipermeable portion of the wall is formed of a semipermeable material that is substantially imperforated or substantially homogenous while remaining substantially impermeable to the composition contained in the core confined within the wall.*

Column 4, paragraph 4.

The passageways formed by the means will generally be regularly shaped, sized, and positioned and may be in the form of discrete holes or a network of cracks or fissures extending over part or all of the dispenser surface. Individually, the passageways are normally minute, usually microscopic, and they constitute an outlet for the solution of the active agent that falls within the *following* maximum and minimum size limitations [described in columns 20–21 of U.S. Pat. No. 3,916,899].

*The size of the passageway means formed in the devices of this invention is designed so that the rate of product delivered, $Q_D/t$, attributed to diffusion in the fluid present in the passageway is always less than the rate of pumping, $Q_P/t$, through the passageway. The expression $Q_D$ is the amount of drug expressed in grams diffusing through the passageway in t time, expressed in hours, and $Q_P$ is the amount of product delivered by pumping in the time t in units of grams/hour. The quantity $Q_P/t$ is determined by the amount of fluid which permeates through the membranes as controlled by the permeability of the membrane and its thickness and the osmotic difference across the membrane. In the devices of the invention, $Q_P/t$ is greater than $Q_D/t$ which assures that the device is essentially an osmotic powered device. By combining the above equations, it is immediately obvious that the product rate of release from the device of the invention is encompassed by the following equation:*

$$\frac{Q_P}{t} = k \frac{A_m}{t_m} \times \text{osmotic pressure} \times \frac{\text{drug solubility}}{1 + \frac{\text{drug solubility}}{\text{drug density}}}$$

*wherein $A_m$ = area of membrane, $t_m$ = thickness of membrane, and wherein k is the permeability coefficient defined as cc of fluid/hr cm² × thickness of membrane/osmotic pressure. The above presentation along with methods for measuring flow rates and the like are described in Encyl. Polymer Sci. Technol., Vol. 9, pages 659 to 688, 1968 published by Interscience Publishers, in Encyl. of Chem. Technol., Vol. 14, pages 345 to 356, 1967, published by Interscience Publishers, Inc., and in Desalination by Reverse Osmosis, Merten, U., pages 15 to 54, 1966, published by the M.I.T. Press, Cambridge, Mass.*

*The operative size of the passageway in any given osmotic device made according to the mode and manner of the invention can easily be ascertained from the immediate equation wherein the maximum size of the passageway is*

$$A_s = \frac{L}{F} \frac{Q_P}{t} \times \frac{1}{D_s}$$

*wherein $A_s$ is the cross sectional area of the passageway, h is the length of the passageway and for a device with a passageway through a membrane it corresponds to the thickness of the membrane, D is the diffusional coefficient of the active agent in the solution osmotically attracted into the device, F is the ratio of mass of active agent delivered per unit time conveniently stated as $Q_Pt$, to the mass of agent or drug $Q_D/t$ delivered in the absence of any measurable osmotic pumping so the ratio of*

$$F = \frac{Q_P/t}{Q_D/t}$$

*is always at least 2 and preferably greater than 10 and usually in a presently/preferred range of from 10 to 1000, wherein S is as previously defined.*

*The size of the passageway is constructed with a minimum size so that size thereof is sufficiently large to essentially prevent hydrostatic pressure P buildup in a device. This minimum size can be determined, for example, for a cylindrical passageway by the following general equation*

$$A_s = \left[ \frac{LV}{t} \times 8 \times \frac{\pi \eta}{\Delta P} \right]^{1/2}$$

*wherein $A_s$ is the cross-sectional area of the passageway, $\pi$ is 3.14, $\eta$ is the viscosity of the solution in the passageway leaving the device, $\Delta P$ is hydrostatic pressure difference between the inside and the outside of the device, at which the device osmotically pumps agent without substantially deforming or rupturing the wall of the device and it is preferably less than 20 atmospheres, L is the length of the passageway and V/t is as previously defined.*

Column 4, paragraph 5.

In the dispensers of the invention, the thickness of the wall may affect the operability of the passageway forming means and in such instances wall thickness will be correlated with the particular passageway forming means to insure that one or more passageways meeting the abovementioned minimum/maximum size limitations are formed timely. Normally the thickness of the wall will be in the range of about 100 to about 500 microns.

The amount of active agent composition present in the device, whether soluble, or a derivative soluble form thereof, is generally non-limited and it is an amount larger than or equal to the amount of the composition that is necessary to osmotically operate the device and on its release from the device, is effective for bringing about the product's desired effect. Since the invention contemplates a variety of devices of various shapes for a variety of uses, there is no critical upper limit on the amount of product incorporated in the device. The lower limit will depend on osmotic activity, the span of the release of the product, and the activity of the product it, being necessary to the maintenance of a zero order release rate that the amount initially present be in excess of the amount that can be dissolved by the water initially inbibed and sufficient to maintain a saturated solution for the span of release. Generally the device will contain from about 0.01% to 90% or higher of a product or a mixture of a product and solute based on the weight of the product or product solute to the volume of the device and the like. Typically the device can be of such size and shape to release 0.01 cc to 5 cc or higher of product contained in the fluid per hour, day, or longer, such as 1 cc to 10 cc of product solution for 1 to 10 days, and the like.

The delivery devices of the invention can take a wide variety of shapes, sizes and forms for administering, for example, the useful agent, drug, or the like at controlled, substantially constant rates to different areas, for example, of the body or to different drug receptor sites or to animal body passages or for administering other active agents to other environments. For example, the invention includes oral drug delivery devices, osmotic implants, osmotic buccal devices, pessaries, prosthesis, artificial glands, cervical rings, intrauterine drug delivery devices of cylindrical, bullet, elliptical, circular, bulbous, loops, bows, or any other geometrical shape that readily lends itself to intrauterine placement; and osmotic ocular drug delivery devices of any convenient geometric shape for comfortable retention in the cul-de-sac of the eye. The general dimensions of an osmotic ocular device can vary with the size of the device and conforming to the amount of drug in the device's drug compartment, the rate at which the drug is to be administered to the eye and by the size of the eye. Satisfactory devices for insertion in the cul-de-sac of the eye generally have a length of 4 to 20 millimeters, a width of 1 to 15 millimeters, and a thinkness of 0.1 to 4 millimeters, a reservoir with a diameter of 1.2 to 14.9 millimeters, and contain from 1 microgram to 100 milligrams of drug or more and the like. The oral osmotic tablets made according to the invention can also be of various conventional sizes such as ³⁄₁₆ in., ⁷⁄₃₂ in., ¹¹⁄₃₂ in., ⁷⁄₁₆ in., ½ in, ¾ in, 1 in, 1¼ in, 1⅓ in, 2⅓ in, 2½ in, and the like smaller or larger dimensions. The oral tablet can also have an elongated shape with a size corresponding to conventional capsule dimensions such as triple zero, double zero, zero, 1 through 8 and the like. Additionally, the novel and useful dispensing device can be used for release of a wide variety of active agents and the term agents as used in this specification and the accompanying claims includes any compound, mixture of compounds, composition of matter or mixture thereof which, when dispensed, produces a predetermined beneficial and useful result. The active agents include pesticides, herbicides, germicides, biocides, algicides, rodenticides, fungicides, insecticides, anti-oxidants, plant growth promotors, plant growth inhibitors, preservatives, surfactants, disinfectants, sterilization agents, catalysts, chemical reactants, medicants, fermentation agents cosmetics, foods, nutrients, food supplements, plant foods, drugs, vitamins, plant minerals, sex sterilants, plant hormones, fertility inhibitors, fertility promotors, air purifiers, microorganism attenuators, and other like agents that benefit man, animals, avians, fish and the environment. Also, all of the dispensing devices are of appropriate known shapes and sizes for implantation, insertion or positioning the desired body cavities, passageways or in the desired environment, such as streams, aquariums, fields, reservoirs, laboratory facilities, manufacturing facilities, transport means and the like.

AS A RESULT OF REEXAMINATION, IT HAS BEEN DETERMINED THAT:

Claims 2-11, having been finally determined to be unpatentable, are cancelled.

Claim 1 is determined to be patentable as amended.

1. An osmotically driven active agent *pump* [dispenser] for *pumping an active agent containing solution into* [use in] an aqueous environment *at a substantially constant rate for an extended period of time after introduction into said environment, said pump* comprising:
   (a) a core *containing an amount* of an osmotically effective pressure generating active agent composition *sufficient to maintain the concentration of said pressure generating composition in solution within the pump at the saturation level for said extended period of time*; and
   (b) a substantially inexpandable wall having a substantially intact surface enclosing the core, said wall being substantially impermeable to the active agent composition [and], *at least a portion of said wall being permeable to water, said water permeable portion* having a controlled *and predetermined* permeability to water and including,
   (c) means responsive to the pressure generated within the [dispenser] *pump* by imbibition of water from the environment by the core through the *water permeable portion of said* wall to create and form at least one exit passageway in situ in the wall through which the active agent composition in solution is pumped osmotically from the core into the environment at a substantially predetermined, substantially constant rate *after the formation of said exit passageway and for said extended period of time.*

New claims 12-32 are added and determined to be patentable.

*12. The pump of claim 1, wherein the in situ formed passagway has a maximum cross-sectional area, $A_s$ defined by:*

$$\frac{L}{F} \times \frac{Q_P}{t} \times \frac{1}{D_S}$$

*wherein L is the length of the passageway, $Q_P/t$ is the mass of agent released from the device per unit time, D is the diffusion coefficient of agent in the dispensed solution, S is the solubility of agent in the fluid and F has a value of from 2 to 1000, said passageway having a minimum area, $A_s$, defined by:*

$$\left[\frac{Lv}{t} \times 8 \times \frac{\pi\eta}{\Delta P}\right]^{\frac{1}{2}}$$

wherein L is the length of the passageway, (v/t) is the volume of agent solution pumped per unit time, $\pi$ is 3.14, $\eta$ is the viscosity of the solution being dispensed and $\Delta P$ is the hydrostatic pressure difference between the inside and the outside of the compartment and having a value of up to about 20 atmospheres.*

*13. An osmotically driven active agent pump for pumping a predetermined amount of an active agent composition to an aqueous environment at a substantially constant rate over an extended period of time comprising:*

*(a) a central unitary core of an osmotic pressure generating active agent composition containing substantially all said predetermined amount of active agent composition to be pumped,*

*(b) an imperforate wall structure surrounding said core, said wall structure being substantially impermeable to the active agent composition, at least a portion of said wall structure being permeable to water, said water permeable portion having a controlled and predetermined permeability to water, and*

*(c) passageway forming means within said wall structure for forming at least one passageway in situ through said wall structure through which active agent composition in saturated solution may be pumped from said core to said aqueous environment at a predetermined, substantially constant rate for an extended period of time after said passageway is formed; said passageway forming means being:*

*(i) responsive to pressure generated within the dispenser by imbibition of water from the environment through the semipermeable wall portion,*

*(ii) adapted to form a total passageway cross sectional area through which said saturated solution may pass at a rate substantially equal to the rate at which water is imbibed through said wall structure, and*

*(iii) adapted to restrict the size of said passageway to a size that will maintain a substantially constant osmotic pressure differential between said core and said aqueous environment for said prolonged period of time.*

*14. In an osmotically driven active agent pump for pumping a predetermined amount of active agent composition to an aqueous environment at a substantially constant rate for an extended period of time comprising:*

*(a) a core of an osmotically effective pressure generating active agent composition surrounded by a wall, said wall being substantially impermeable to the active agent composition, with at least a portion of said wall being permeable to water, said water permeable portion having a predetermined permeability to water, said core containing an amount of pressure generating active agent composition sufficient to maintain the solution formed within said wall saturated for said extended period of time,*

*(b) passageway means in said wall sized to permit active agent composition in saturated solution within said wall structure to be osmotically pumped therefrom at a substantially constant rate for an extended period of time; the improvement which comprises:*

*pressure-responsive means within said wall structure for forming said passageway means in situ after the pump is placed in said aqueous environment.*

*15. In an osmotically driven active agent pump which delivers a solution of active agent for a substantial period of time at a substantially constant rate as a result of a substantially constant osmotic pressure differential maintained between the interior of said dispenser and an aqueous environment to which it is exposed, said pump comprising:*

*(a) a core of an osmotically effective pressure generating active agent composition surrounded by,*

*(b) a substantially inexpendable wall provided with passageway means providing fluid communication between the interior of said pump and said aqueous environment, said wall being substantially impermeable to the active agent composition and having at least a portion which is permeable to water, said water permeable portion having a predetermined permeability to water,*

*(c) said passageway means in said wall being sized such that the mass of active agent delivered per unit time as a result of osmotic pressure induced flow through said passageway means is at least 2 times greater than the mass of active agent delivered per unit time by passive diffusion from solution in said passageway means;*

*the improvement wherein said wall structure is imperforate prior to exposure to said aqueous environment and is capable of forming said passageway means in situ in said aqueous environment in response to the increase in pressure within said pump caused by the osmotic pressure differential between the aqueous environment and the interior of said pump whereby the desired delivery rate over a prolonged period of time can be obtained without the necessity of preforming the passageway means through said wall structure.*

*16. The pump of claim 15, wherein the in situ formed passageway has a maximum cross-sectional area, $A_s$ defined by:*

$$\frac{L}{F} \times \frac{Q_P}{t} \times \frac{1}{D_S}$$

*wherein L is the length of the passageway, $Q_P/t$ is the mass of agent delivered from the device per unit time, D is the diffusion coefficient of agent in the delivered solution, S is the solubility of agent in the fluid and F has a value of from 2 to 1000, said passageway having a minimum area, $A_s$, defined by:*

$$\left[\frac{Lv}{t} \times 8 \times \frac{\pi\eta}{\Delta P}\right]^{1/2}$$

*wherein L is the length of the passageway, (v/t) is the volume of agent solution dispensed per unit time, $\pi$ is 3.14, $\eta$ is the viscosity of the solution being dispensed and $\Delta P$ is the hydrostatic pressure difference between the inside and the outside of the compartment and having a value of up to about 20 atmospheres.*

*17. The pump of claims 1, 12, 13, 14, or 15 wherein the total active agent composition content to be pumped is contained in a unitary core element and said core element constitutes at least 90% by weight of said dispenser.*

*18. An osmotically driven active agent pump for pumping an osmotic pressure generating active agent containing solution to an aqueous environment for an extended period of time at a substantial constant flow rate comprising:*

*(a) an imperforate wall structure defining a hollow enclosure, said wall structure being substantially im-* permeable to said osmotic pressure generating active agent containing composition and at least a portion of said wall structure being permeable to water, said water permeable portion having a predetermined permeability to water;

(b) a core of an osmotic pressure generating active agent composition enclosed by and substantially filling said enclosure, the volume of said core being predetermined to contain an amount of osmotic pressure generating active agent composition sufficient to maintain the concentration of the osmotic pressure generating composition in the solution formed within said enclosure at the saturation level for said extended period of time and (c) passageway forming means in said wall structure for forming fluid flow passageway means through said wall structure, the passageway means formed being maintained at a size such that the mass of active agent composition in solution delivered per unit time over said extended perod of time as a result of osmotic pressure induced flow through said passageway means is at least 2 times greater than the mass of active agent delivered per unit time by passive diffusion from solution is said passageway means; said passageway forming means being responsive to pressure generated within said enclosure by controlled imbibition of water through said water permeable portion of said wall structure to form and maintain said passageway means at said size.

19. The pump of claims 1, 15, 16, or 18 wherein the pressure induced flow of active agent composition is from 10–1000 times greater than the diffusional delivery rate.

20. The pump of claims 1, 12, 13, 14, 15, 16 or 18 wherein said core has a circular cross section having a diameter of at least 1.2 mm.

21. The pump of claims 1, 12, 13, 14, 15, 16 or 18 wherein the active agent composition in solution exhibits an osmotic pressure that is significantly greater than the osmotic pressure of the aqueous environment.

22. The pump of claims 1, 12, 13, 14, 15, 16 or 18 wherein the active agent is a drug.

23. The pump of claims 1, 12, 13, 14, 15, 16 or 18 wherein the composition in solution exhibits an osmotic pressure of about 20,000 to about 40,000 kPa.

24. The pump of claims 1, 12, 13, 14, 15, 16 or 18 wherein the wall is about 100 to about 500 microns thick.

25. The pump of claims 1, 12, 13, 14, 15, 16 or 18 wherein the means is an inherent property of the material forming the wall.

26. The pump of claims 1, 12, 13, 14, 15, 16 or 18 wherein the means is sites of structural weakness in the wall.

27. The pump of claims 1, 12, 13, 14, 15, 16 or 18 wherein the means is sites of structural weakness in the wall and the sites are the result of incorporating a foreign material into the material forming the wall, forming the wall from mutually incompatible polymers, treating the wall thermally, solvent crazing the wall, or subjecting the wall to irradiation.

28. The pump of claims 1, 12, 13, 14, 15, 16 or 18 wherein there is more than one passageway and the passageways are irregularly shaped, sized, and positioned.

29. The pump of claims 1, 12, 13, 14, 15, 16 or 18 wherein the passageway is in the form of a network of cracks extending over at least a part of the surface of the dispenser.

30. The pump of claims 1, 12, 13, 14, 15, 16 or 18 wherein the passageway is in the form of a plurality of discrete holes.

31. The pump of claims 12 or 16 wherein the composition in solution exhibits an osmotic pressure of about 20,000 to about 40,000 kPa, the wall structure through which the passageway means extends is from 100 to 500 microns thick and the pressure differential between the interior of the pump and the environment after the passageway means are formed is no greater than 20 atmospheres.

32. The pump of claims 1, 13, or 14, wherein the mass of active agent delivered per unit of time over said extended period of time as a result of osmotic pressure induced flow through said exit passageway is at least 2 times greater than the mass of active agent delivered by diffusion from the solution in said passageway.

* * * * *